United States Patent [19]
Hershenson et al.

[11] Patent Number: 5,004,605
[45] Date of Patent: Apr. 2, 1991

[54] LOW PH PHARMACEUTICAL COMPOSITIONS OF RECOMBINANT BETA-INTERFERON

[75] Inventors: Susan Hershenson, San Francisco; Jody Thomson, Albany, both of Calif.

[73] Assignee: Cetus Corporation, Emeryville, Calif.

[21] Appl. No.: 131,375

[22] Filed: Dec. 10, 1987

[51] Int. Cl.$^5$ .............................................. C07K 15/26
[52] U.S. Cl. .................................. 424/85.6; 530/351
[58] Field of Search ...................... 424/85.6; 530/351

[56] References Cited

U.S. PATENT DOCUMENTS

| | | |
|---|---|---|
| 4,289,689 | 9/1981 | Friesen et al. . |
| 4,343,735 | 8/1982 | Menge et al. . |
| 4,450,103 | 5/1984 | Konrad et al. . |
| 4,460,574 | 7/1984 | Yabrov . |
| 4,462,940 | 7/1984 | Hanisch et al. . |
| 4,496,537 | 1/1985 | Kwan . |
| 4,507,281 | 3/1985 | Asculai et al. . |
| 4,530,787 | 7/1985 | Shaked et al. . |
| 4,604,377 | 8/1986 | Fernandes et al. . |
| 4,606,917 | 8/1986 | Eppstein ............................ 424/85.6 |
| 4,645,830 | 2/1987 | Yasushi et al. . |
| 4,647,454 | 3/1987 | Cymbalista . |
| 4,675,183 | 6/1987 | Kato et al. . |
| 4,675,184 | 6/1987 | Hasegawa et al. . |
| 4,680,175 | 7/1987 | Estis et al. ........................ 424/85.6 |

FOREIGN PATENT DOCUMENTS

| | | |
|---|---|---|
| 0092918 | 11/1983 | European Pat. Off. . |
| 0123291 | 10/1984 | European Pat. Off. . |
| 0133767 | 3/1985 | European Pat. Off. . |
| 0135171 | 3/1985 | European Pat. Off. . |
| 0168008 | 1/1986 | European Pat. Off. . |
| 0231132 | 8/1987 | European Pat. Off. . |
| 0196203 | 9/1987 | European Pat. Off. . |
| 0257890 | 3/1988 | European Pat. Off. . |
| 33252238 | 1/1985 | Fed. Rep. of Germany . |
| 59-10524 | 7/1984 | Japan . |
| 61-293926 | 4/1986 | Japan . |

OTHER PUBLICATIONS

Billiau et al., Antimicrobial Agents and Chemotherapy, vol. 16, No. 1, pp. 49–55, 1979.
James Sedmak et al., *Methods in Enzymology*, 78:591–595 (1977).
J. W. Heine et al., *Archives of Virology*, 57:185–188 (1978).
U.S. Ser. No. 923,425, filed Oct. 27, 1986.

*Primary Examiner*—Margaret Moskowitz
*Assistant Examiner*—Keith C. Furman
*Attorney, Agent, or Firm*—Philip L. McGarrigle, Jr.; Leona Lauder; Albert P. Halluin

[57] ABSTRACT

Stable pharmaceutical compositions suitable for parenteral administration to mammals are prepared which are in a pH range of about 2 to about 4 and comprise a therapeutically effective amount of a recombinant interferon-$\beta$ protein (IFN-$\beta$) dissolved in an inert carrier medium comprising as a stabilizer/solubilizer an effective amount either of glycerol or of polyethylene glycol polymers having an average molecular weight from about 190 to about 1600 daltons. Further disclosed and claimed are methods for extracting IFN-$\beta$ from a microbial host transformed to produce it and then purifying and formulating said IFN-$\beta$ and methods for screening for other polyhydric non-detergent stabilizer/solubilizers or combinations thereof as solubilizer/stabilizers for pharmaceutical compositions of IFN-$\beta$.

16 Claims, No Drawings

LOW PH PHARMACEUTICAL COMPOSITIONS OF RECOMBINANT BETA-INTERFERON

FIELD OF THE INVENTION

This invention is in the field of biochemical engineering. More particularly, the invention concerns improved pharmaceutical compositions of biologically active recombinant beta-interferon (IFN-$\beta$) protein which are suitable for therapeutic administration to humans.

BACKGROUND OF THE INVENTION

Naturally occurring interferons (IFNs) are species-specific proteins, often glycoproteins, produced by various cells upon induction with viruses, double stranded RNAs, other polynucleotides, antigens and mitogens. Interferons exhibit multiple biological activities such as antiviral, antiproliferative, immunomodulatory and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as $\alpha$, $\beta$ and $\gamma$ interferons. These are reported to be different proteins coded for by distinct structural genes.

Native human $\beta$-interferon (HuIFN-$\beta$) is generally produced by superinducing human fibroblast cultures with poly-IC (poly-riboinosinic acid and polyribocytidylic acid) and isolating and purifying the HuIFN-$\beta$ thus produced by chromatographic and electrophoretic techniques. Proteins or polypeptides which exhibit native $\beta$-interferon properties may also be produced using recombinant DNA technology by extracting poly-A-rich 12S messenger RNA from virally induced human cells, synthesizing double-stranded c-DNA using the m-DNA as a template, introducing the c-DNA into an appropriate cloning vector, transforming suitable microorganisms with the vector, harvesting the bacteria and extracting the HIFN-$\beta$ therefrom. Nagola, S. et al., Nature, 284:316 (1980); Goeddel, D. V. et al., Nature, 287:411 (1980); Yelverton, E. et al., Nuc. Acid Res., 9:731 (1981); Streuli, M. et al., Proc. Nat'l Acad. Sci. (U.S.), 78:2848 (1981); European Pat. Application No. 28033, published May 6, 1981; 321134, published July 15, 1981; 34307 published Aug. 26, 1981; and Belgian Patent No. 837379, issued July 1, 1981 described various currently used methods for the production of $\beta$-interferon employing recombinant DNA techniques. The expressed proteins or polypeptides have been purified and tested and have been found to exhibit properties similar to those of native IFNs. Bacterially produced IFNs thus appear to have potential therapeutic use as antiviral and anti-tumor agents and the production of IFNs by such bacterial fermentations is expected to yield sufficiently large quantities of IFN at a relatively low cost for clinical testing.

Further, HuIFN-$\beta$ genes have been altered by, for example, oligonucleotide-directed mutagenesis to produce IFN-$\beta$ protein analogs thereof, such as the human recombinant cysteine-depleted or cysteine-replaced interferon-$\beta$ analogs (muteins) disclosed in U.S. Pat. No. 4,588,585 issued May 13, 1986 to Mark et al. Specifically disclosed in that patent is the recombinant IFN-$\beta$ mutein wherein the cysteine at position 17 is replaced by a neutral amino acid such as serine. The latter IFN-$\beta$ mutein is IFN-$\beta_{ser17}$.

Procedures for recovering and purifying bacterially produced IFNs are described in U.S. Pat. Nos. 4,450,103; 4,315,852; 4,343,735; and 4,343,736; and Derynck et al., Nature (1980) 287:193–197 and Scandella and Kornberg, Biochemistry, 10:4447 (1971).

E. coli expressed recombinant IFN-$\beta$ and analogs thereof are insoluble in solutions which are at a pH range of 6 to 9. Therefore, various processes and additives have been devised to solubilize these proteins. Several methods currently available for the preparation, recovery and purification of bacterially produced proteins are listed immediately below.

U.S. Pat. No. 4,315,852 to Leibowitz et al., describes a method for the acid extraction of leukocyte interferon from bacterial cells and neutralization of the extractant to obtain the interferon.

U.S. Pat. No. 4,343,735 to Menge et al., teaches a process for the purification of interferon by partitioning it in an aqueous multi-phase system in the presence of ion exchangers which are soluble in the system and are derivatives of polyethers.

U.S. Pat. No. 4,343,736 to Uemura et al. discloses a method for recovering interferon by absorption of water-insolubilized heparin and then eluting the interferon with an aqueous solution of an inorganic salt and chondroitin sulfate.

U.S. Pat. No. 4,289,689 to Friesen et al. discloses how to recover and purify human native $\beta$-interferon by use of affinity chromatography and high pressure liquid chromatography.

U.S. Pat. No. 4,364,863 to Leibowitz et al. describes a method of extracting fibroblast interferon from bacteria using a low pH followed by a high pH extraction procedure.

U.S. Pat. No. 4,450,103 to Konrad et al. discloses solubilizing the protein in an aqueous medium with an appropriate solubilizing agent, extracting the protein from the aqueous medium with 2-butanol or 2-methyl-2-butanol, and precipitating the protein from the alcohol phase.

U.S. Pat. No. 4,530,787 to Shaked et al. describes a process for oxidizing recombinant proteins such as IFN-$\beta$ selectively and stoichiometrically using o-iodosobenzoic acid to ensure that the protein will be functionally equivalent to its native counterpart.

Many heterologous proteins are precipitated intracellularly in the form of refractile or inclusion bodies which appear as bright spots visible within the enclosure of the cell under a phase contrast microscope at magnifications down to 1000 fold. See e.g., Miller et al., Science (1982) 215:687–690; Cheng, Biochem. Biophys. Res. Comm., (1983) 111:104–111; Becker et al., Biotech. Advs. (1983) 1:247–261; Kleid et al., ch. 25 in Developments in Industrial Microbiology, Vol. # 25, pp. 317–325 (Society for Industrial Microbiology, Arlington, Va., 1984); Marston et al., Bio/Technology (Sept., 1984), pp. 800–804.

Purification and activity assurance of precipitated heterologous proteins is also described by U.S. Pat. Nos. 4,511,502; 4,511,503; 4,512,922; 4,599,127 and 4,518,526; and EP No. 114,506.

Wang et al., J. Parenteral. Drug Assoc., 34, 452–462 (1980) provides a review of excipients and pHs for parenteral products used in the U.S. Table I therein under section II entitled "Solubilizers, Wetting Agents or Emulsifiers" lists among other excipients polyethylene glycol 300 and glycerin.

U.S. Pat. No. 4,647,454 to Cymbalista et al. discloses a method of stabilizing human fibroblast interferon with polyvinyl pyrrolidone.

U.S. Pat. No. 4,460,574 to Yabrov discloses a pharmaceutical composition comprising native human α- and β-interferons used for rectal or urogenital treatment of human interferon-sensitive diseases.

U.S. Pat. No. 4,462,940 to Hanisch et al. ('940 patent) discloses a process for formulating interferon by mixing the interferon and a protein stabilizer, such as normal serum albumin, at a pH of about 10.5 to 12.5 for 5 minutes and then adjusting the pH to 7.5 to obtain a soluble mixture.

Copending, commonly owned, U.S. application Ser. No. 775,751, filed Sept. 13, 1985 entitled "An Improved Formulation for Lipophilic Proteins" outlines a high pH and a low pH process for removing and purifying lipophilic recombinant proteins, such as human IFN-β and interleukin-2, from host strains to yield a protein preparation which may be formulated into a stable pharmaceutical composition. Said composition carrying a therapeutically effective amount of the biologically active lipophilic protein dissolved in a not-toxic, inert, therapeutically compatible aqueous-based carrier medium at a pH of 6.8 to 7.8 also contains a stabilizer for the protein, such as human serum albumin, human serum albumin and dextrose, or human plasma protein fraction.

Copending, commonly owned, U.S. application Ser. No. 780,551, filed Sept. 26, 1985, entitled "Stable Formulation of Biologically Active Proteins for Parenteral Injection," discloses pharmaceutical compositions containing IFN-β or interleukin-2 dissolved in a stable carrier medium at pH 7.0 to 8.0 stabilized with sodium laurate.

Copending, commonly owned, U.S. application Ser. No. 749,955 filed June 26, 1985, and 866,459 filed May 21, 1986 (Katre et al.), disclose pharmaceutical compositions wherein recombinant IFN-β, IL-2 or an immunotoxin is dissolved in an aqueous carrier medium at pH 6 to 8 without the presence of a solubilizing agent. The protein is solubilized by selectively conjugating it via a coupling agent to a water-soluble polymer selected from polyethylene glycol homopolymers or polyoxyethylated polyols.

Japanese Laid-Open Patent Application (Kokai) No. 59-10524 (published Jan. 20, 1984) entitled "An Interferon Composition and a Method of Manufacturing the Same" discloses a micelle solution for rectal administration prepared by mixing (a) an unsaturated fatty acid, (b) a polyoxethylene fatty acid ester, alkyl polyoxethylene ether or sucrose fatty acid ester, (c) water and (d) interferon.

European Patent Application Publication No. 135,171 (published Mar. 27, 1985) discloses pseudomonophase, microemulsion compositions for topical application of interferons, preferably leukocyte interferon A. The compositions comprise a therapeutically effective amount of interferon, 30–70% by volume of a surface active agent having a hydrophilic-lipophilic balance (HLB) of from 12–15 and dual solubility in water/oil; 5–45% of a vegetable oil; and 5–45% water. The surface active agents disclosed therein are polyethylene glycol derivatives of castor oil composed on average of 25–36 moles of ethylene oxide per mole of castor oil. Such an oil-based microemulsion is not stable and subject to phase separation.

U.S. Pat. No. 4,507,281 discloses compositions comprising about $10^4$ to $10^6$ I.U. of human leukocyte interferon, about 1% to 5% by weight of a non-ionic surface active agent having at least one ether or amide linkage, and a physiologically acceptable carrier.

Copending, commonly owned U.S. Ser. No. 923,423, filed Oct. 27, 1986 and 100,679, filed Sept. 29, 1987, both entitled "Pharmaceutical Compositions of Recombinant Beta-Interferon and Formulation Processes" disclose and claim stable, pharmaceutical compositions of recombinant interferon-beta (IFN-β) comprising as solubilizer/stabilizers one or more non-toxic biocompatible non-ionic polymeric detergents or a combination of one or more such non-ionic detergents and an additional solubilizing and/or stabilizing agent, such as, sodium dodecyl sulfate or glycerol. Said applications further disclose and claim methods of extracting IFN-β from the disruptate of a host organism transformed to produce it and purifying the IFN-β wherein the last purification step prior to formulation is a desalting step performed at a pH range or about 8.5 to about 10 wherein the elution buffer contains a fatty acid salt having from about 10 to about 12 carbons, and wherein the pH of the desalted IFN-β pool is lowered to about 2 to about 4 thereby precipitating the fatty acid salt. The precipitated salt, preferably sodium laurate, is removed by centrifugation and filtration, and the filtrate is formulated with the non-ionic detergent containing solubilizer/stabilizers discussed therein.

There remains a need in the art for alternative formulations of biologically active, recombinant beta-interferons, preferably that are alternatives to those containing non-IFN-β protein, such as albumin. The present invention meets such a need.

SUMMARY OF THE INVENTION

This invention provides for stable pharmaceutical compositions of matter suitable for parenteral administration to mammals that are a pH range of from about 2 to about 4, comprising a therapeutically effective amount of a recombinant interferon-β protein (IFN-β) dissolved in an inert carrier medium comprising as a stabilizer/solubilizer an effective amount either of glycerol or of polyethylene glycol polymers having an average molecular weight from about 190 to about 1600 daltons, more preferably from about 190 to about 420 daltons, and still more preferably from about 285 to about 315 daltons.

The volume to volume (v/v) concentration range for said solubilizer/stabilizers in said compositions is preferably from about 5 to about 50%, and more preferably about 25%.

The IFN-β is most preferably IFN-$β_{ser17}$.

The compositions further comprise an appropriate buffer, preferably phosphate, at a concentration from about 1 to about 50 mM, more preferably from about 10 mM to about 25 mM.

The invention further provides for methods of preparing stable, pharmaceutical compositions of recombinant interferon-β (IFN-β) protein comprising the steps of:

(a) extracting the IFN-β from the disruptate of a host organism transformed to produce the protein;

(b) purifying the IFN-β using as the last purification step a desalting step at a pH range of about 8.5 to about 10 employing an elution buffer containing a fatty acid salt having a carbon chain containing from about 10 to about 12 carbons (preferably laurate) to form a desalted pool;

(c) lowering the pH of the desalted pool to about 2 to about 4, thereby precipitating the fatty acid salt;

(d) removing the precipitated salt from the pool by centrifugation and filtration; and (e) adding to the desalted pool an effective amount either of glycerol or of polyethylene glycol polymers having an average molecular weight from about 190 to about 1600 daltons to stabilize/solubilize the IFN-$\beta$.

The invention still further concerns a method of extracting recombinant interferon-$\beta$ (IFN-$\beta$) from a bacterial host transformed to produce it and then purifying and formulating said IFN-$\beta$ comprising the steps of:

(a) growing the transformed bacterial host in an appropriate fermentation medium;

(b) concentrating the bacterial host in the fermentation medium;

(c) disrupting the cell wall and cell membrane of the bacterial host;

(d) removing greater than 99% by weight of the salts from said disruptate by diafiltration or centrifugation;

(e) redisrupting the desalted disruptate;

(f) adding a material to the disruptate to increase the density or viscosity of, or to create a density or viscosity gradient in, the liquid within the disruptate containing refractile material;

(g) separating the refractile material from the cellular debris by high-speed centrifugation;

(h) solubilizing the refractile material in an aqueous buffer containing a reducing agent;

(i) extracting the solubilized refractile material with 2-butanol or 2-methyl-2-butanol;

(j) isolating said refractile material from the 2-butanol or 2-methyl-2-butanol to produce an IFN-$\beta$ particle pellet;

(k) solubilizing the particle pellet with an aqueous solution of sodium dodecyl sulfate at an IFN-$\beta$ to sodium dodecyl sulfate ratio of about 1:3 to form a solution;

(l) reducing the solubilized IFN-$\beta$;

(m) purifying the reduced IFN-$\beta$ by chromatography;

(n) oxidizing the IFN-$\beta$ from step (m);

(o) further purifying the oxidized IFN-$\beta$ by gel chromatography and collecting the eluate containing the purified IFN-$\beta$;

(p) desalting the purified IFN-$\beta$ eluate in a desalting column equilibrated and run in sodium laurate at a pH from about 9.0 to about 9.8;

(q) lowering the pH of the eluate to a pH of from about 2 to about 4;

(r) centrifuging and filtering the eluate to remove the precipitate; and (s) adding to the filtrate from step (r) an effective amount either of glycerol or of polyethylene glycol polymers having an average molecular weight of from about 190 to about 1600 daltons to solubilize and stabilize the IFN-$\beta$.

This invention further provides for methods of screening for polyhydric non-detergent solubilizer/stabilizers or combinations thereof wherein a representative screening method comprises the steps of:

(a) passing extracted, purified recombinant IFN-$\beta$ in 0.1% SDS on a desalting column equilibrated in 0.1% sodium laurate in an elution buffer at pH 9.0–10.0;

(b) lowering the pH of the eluate with an appropriate acidic agent to from about pH 2 to about pH 4;

(c) adding an appropriate concentration of a candidate polyhydric non-detergent solubilizer/stabilizer or combination of polyhydric non-detergent solubilizer/stabilizers;

(d) allowing said solution to stand for from about twenty-four hours to about one month at about 4° C.; and (e) observing whether the solution remains stable or not. If the solution remains stable, and the recombinant IFN-$\beta$ retains its bioactivity, the polyhydric non-detergent candidate or combination of such candidates is considered to be within the scope of the solubilizer/stabilizers of this invention.

DETAILED DESCRIPTION OF THE PREFERRED EMBODIMENTS

The term "recombinant $\beta$-interferon," designated as IFN-$\beta$, preferably human IFN-$\beta$, refers to fibroblast interferon having biological activity comparable to native IFN-$\beta$, prepared by recombinant DNA techniques as described in the art. In general, the gene coding for interferon is excised from its native plasmid and inserted into a cloning vector to be cloned and then into an expression vector, which is used to transform a host organism, preferably a microorganism, and most preferably *E. coli*. The host organism expresses the foreign interferon gene under certain conditions to produce IFN-$\beta$. More preferably, the IFN-$\beta$ is a mutein as described in U.S. Pat. No. 4,588,585, in which the cysteine normally occurring at position 17 of the wild-type or native molecule has been replaced by a neutral amino acid, such as, serine or alanine. Most preferably, the IFN-$\beta$ mutein is IFN-$\beta_{ser17}$.

The precise chemical structure of the IFN-$\beta$ protein will depend on a number of factors. As ionizable amino and carboxyl groups are present in the molecule, a particular IFN-$\beta$ protein may be obtained as an acidic or basic salt, or in neutral form. All such preparations which retain their bioactivity when placed in suitable environmental conditions are included in the definition of IFN-$\beta$ proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of IFN-$\beta$ protein herein so long as the biological activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy biological activity do not remove the protein sequence from the definition.

The pharmaceutical compositions of this invention provide a means of maintaining recombinant IFN-$\beta$ in soluble form and thereby stabilizing it by use of one or more solubilizer/stabilizers of this invention. The most difficult IFN-β solubility problems are those that occur with nonglycosylated IFN-β produced by a transformed bacterial host, most notably E. coli. Therefore, the pharmaceutical compositions of this invention are especially useful in solubilizing/stabilizing nonglycosylated IFN-β produced in E. coli, and it is preferred that the recombinant IFN-β of the pharmaceutical compositions of this invention be of such origin.

The term "primary solubilizing agent" is defined herein to mean a solubilizing agent, preferably a detergent and/or chaotrope, which is used to solubilize the IFN-β from the refractile bodies in the abbreviated or expanded front-end processes of purifying IFN-β described infra.

As used herein the term "transformed" in describing host microorganism cell cultures denotes a microorganism that has been genetically engineered to produce IFN-β that possess biological activity comparable to native IFN-β. Bacteria are preferred microorganisms for producing IFN-β. E. coli is particularly preferred.

"Chaotropic environment" refers to an environment in which proteins are denatured or changed from their ordinary conformations. Chaotropic environments may be engendered by the presence of suitabl concentrations of chaotropic agents, as described below, or may be the result of heat or pH alterations. The resultant environments are capable of disrupting hydrogen bonding in the protein and altering the thermodynamics of the surroundings in such a way that alternate three-dimensional conformations are preferred in the chaotropic environment to those found in more physiologically compatible environments.

The term "chaotropic agent" refers to a compound or compounds which, in aqueous solution and in a suitable concentration, engender a chaotropic environment and are capable of denaturing IFN-β. Guanidine salts (e.g., the hydrochloride) and alkali metal thiocyanates (e.g., sodium thiocyanate), are examples of chaotropic environments that will dissolve and denature IFN-β.

"Reducing conditions" are those required to place or maintain the IFN-β in reduced form with respect to the cysteine residues. These conditions can most simply be provided by use of a suitable reducing agent (especially a thiol-containing reducing agent), or if the IFN-β is already reduced (e.g., in the cellular environment), exclusion of air and oxidation catalysts or reagents may suffice.

"Elution buffer" is herein defined as a solution used to remove adsorbed species from a chromatographic column wherein said solution is selected or prepared to minimize changes in hydrogen ion concentration which would otherwise occur as a result of a chemical reaction.

The term "mammals" is defined herein to mean an animal belonging to the class Mammalia which class includes the family Hominidae (humans).

"Inert" is defined herein to mean chemically inactive.

As used herein, the term "solubilizer/stabilizer" as applied to the recombinant IFN-β formulations refers to essentially non-toxic and non-immunogenic compositions which alone or in combination act not only to stabilize the IFN-β against denaturation and loss of biological activity, but also to solubilize the lipophilic protein in an aqueous medium so that the pharmaceutical formulation constitutes a stable aqueous solution of IFN-β protein in a pH range from about 2 to about 4, preferably from about 2.5 to about 3.5, and more preferably about 3.0, from which the protein will not precipitate preferably for at least one month at about 4° C. The stabilizer/solubilizer compositions of the invention are either a solubilizing/stabilizing effective amount of glycerol or of polyethylene glycol polymers having an average molecular weight from about 190 to about 1600 daltons.

More preferably, the stabilizer/solubilizers of this invention that comprise polyethylene glycol homopolymers (PEGs) are of an average molecular weight of from about 190 to 420 daltons, and still more preferably from about 285 to about 315 daltons. Such molecular weight ranges are correlated with the empirical formula for polyethylene glycol as follows:

$HOCH_2(CH_2OCH_2)_nCH_2OH$ where n represents the average number of oxyethylene groups and is related to the molecular weight of such compounds such that

| n | Average Molecular Weight |
|---|---|
| 3 | 190–210 |
| 5–6 | 285–315 |
| 8–10 | 380–420 |
| 11–13 | 570–613 |
| 20–24 | 950–1050 |
| 30–36 | 1400–1600 |

As indicated above the most preferred PEGs are those wherein n=5–6. Such compounds are commercially known by the grade name PEG 300. Herein PEG 300 is considered to be synonymous with polyethylene glycol compounds that have an average molecular weight of about 285–315 wherein n=5–6.

Glycerol, another stabilizer/solubilizer that can be used, is a trihydric sugar alcohol having the formula

Glycerol is also known as glycerin when used in pharmaceutical compositions.

As indicated above, it is preferred that the stabilizer/solubilizers of this invention be in a concentration range (v/v) of from about 5% to about 50%, more preferably about 25%. At such concentrations, glycerol and the PEGs described herein as stabilizer/solubilizers are considered non-lyophilizable. Therefore, the compositions of this invention are preferably in liquid form.

Further, the concentration of the stabilizer/solubilizers of this invention varies with the concentration of IFN-β in the formulation. For example, a high dosage formulation of IFN-β is that which contains about 1 to about 2 mg/ml of IFN-β in the final container vial (2 to 4 × 10⁸ units per mg). A normal dosage formulation has about 0.25 mg/ml of IFN-β in the final container vial (0.5 × 10⁸ units per mg); whereas, a low dosage formulation has about 0.125 mg/ml of IFN-β in the final container vial (0.25 × 10⁸ units per mg). Generally lower dosage formulations of IFN-β require lower concentration ranges of the stabilizer/solubilizers, whereas higher dosage formulations require higher concentration ranges.

The preferred range of recombinant IFN-β in the compositions of this invention is from about 0.05 mg/ml to about 10 mg/ml, more preferably 0.1 mg/ml to about 5 mg/ml, and still more preferably 0.1 mg to about 2.0 mg/ml.

The liquid formulations are preferably maintained at a temperature range of from about −70° C. to about +10° C. The frozen formulations are preferably maintained at a temperature range of about −70° C. to about −20° C., whereas the stabilized liquid formulations are preferably maintained at a normal refrigeration range, preferably from about +2° C. to about +8° C.

The liquid formulations of this invention comprise:
(1) recombinantly produced, purified IFN-$\beta$;
(2) a solubilizing/stabilizing effective amount of glycerol or of polyethylene glycol compounds (PEGs) having an average molecular weight from about 190 to about 1600 daltons; and
(3) a small amount of buffer that maintains the formulations at a pH range of from about 2 to about 4.

The buffer selected to maintain the formulations at the above-described pH ranges is at a concentration from about 1 to about 50 mM, more preferably from about 10 to about 25 mM. Preferably, the buffers for the pharmaceutical compositions of this invention are selected from the group consisting of phosphoric acid, glycine and citric acid, and more preferably, the buffer is phosphate.

The compositions can further comprise an additional stabilizing agent, such as, a carbohydrate, for example, sucrose, dextrose, dextran, mannitol, sorbitol, inositol, fructose, galactitol, xylitol, lactose, and trehalose; or a non-carbohydrate, for example, human serum albumin (HSA) which can be used alone or in combination with a carbohydrate stabilizing agent. Such stabilizing agents are preferably in a concentration (weight/weight) range of from about 0.025% to about 10%, preferably from about 0.05% to about 7%, and more preferably from about 0.1% to about 5%.

The compositions of this invention can further comprise an effective amount of a preservative and/or an antimicrobial agent.

A preferred process for preparing the IFN-$\beta$ formulations of this invention comprises the steps of: (a) extracting the recombinant betainterferon (IFN-$\beta$) from the disruptate of a host organism trasformed to produce the protein; (b) purifying the IFN-$\beta$ protein using as the last purification step a desalting or diafiltration step at a pH range of about 8.5 to 10 employing a transfer component; (c) lowering the pH of the desalted pool with an appropriate acidic agent to a pH of about 2 to about 4; (d) removing the precipitated transfer component by centrifugation and filtration; and (e) adding to the desalted pool an effective amount either of glycerol or of PEGs having an average molecular weight from about 190 to about 1600 daltons to stabilize/solubilize the IFN-$\beta$.

The transfer component of step (b) is employed to replace the primary solubilizing agent, such as sodium dodecyl sulfate (SDS), used in the extraction and purification of the recombinant IFN-$\beta$ from the host microorganisms. The transfer component is preferably a detergent or chaotrope that is milder than the stronger primary solubilizing agent, which thereby allows for the diafiltration or desalting step to be performed at a lower pH range than would otherwise be successful. Copending, commonly owned U.S. Ser. Nos. 923,423 and 100,679, filed respectively on Oct. 27, 1986 and Sept. 29, 1987, explain the dynamics of the phenomenon and are herein incorporated by reference.

Examples of such detergent/chaotropes for use as transfer components include fatty acid salts having carbon chains of from about 10 to 13 carbons, preferably 11 to 12 carbons and most preferably 12 carbons. It is preferred that the fatty acid salt be a laurate salt and most preferred that such laurate salt be sodium laurate.

The concentration range of said transfer component in a elution buffer, preferably a low ionic strength elution buffer, is from about 0.05% to about 2%, preferably 0.1% to 1% (volume/volume).

The representative process described in Example 1 infra was found to remove the sodium laurate transfer component to levels below the detection limit (that is, approximately 10 moles of laurate per mole of IFN-$\beta$) of an assay employing a standard protein RP-HPLC system with low wavelength UV detection.

For purposes of practicing the present invention, bacteria are the preferred microorganism hosts, with *E. coli* being the most preferred.

In general, the recovery, purification and formulation processes herein involve fermenting the host organism transformed to express the IFN-$\beta$, disrupting the cell wall and cell membrane of the host organism, separating the refractile material containing the recombinant IFN-$\beta$ from the rest of the cellular debris, solubilizing the refractile material in an aqueous buffer under reducing conditions, extracting the IFN-$\beta$ with 2-butanol or 2-methyl-2-butanol, subjecting the extracted IFN-$\beta$ to chromatographic purification, and then diafiltering or desalting, preferably desalting, the IFN-$\beta$ to remove the primary solubilizing agent optionally using a suitable transfer component and formulating as described above.

Flow Chart 1 outlines a preferred process of this invention for extracting, purifying and stabilizing the IFN-$\beta$ protein wherein sodium dodecyl sulfate (SDS) is used as the primary solubilizing agent, and wherein sodium laurate is used as a transfer component during a desalting step on a Sephadex ® G-25 desalting column.

| FlowChart 1 | |
|---|---|
| Fermentation | |
| Cell concentration | |
| Cell wall and membrane disruption | homogenization |
| Diafiltration | 5 mM EDTA |
| Redisruption | 2 mM EDTA; 1% octanol (v/v); homogenization |
| Sucrose suspension | 15–23% sucrose (w/w) |
| Centrifugation | 10,000–15,000 xg |
| Paste solubilization | 2% SDS; phosphate buffered saline |
| Reduction | 10 mM DTT; 2% SDS; 2 mM EDTA; pH 9; heat to 50° C. for 10 min. under nitrogen; cool to about 25° C.; adjust pH to 7.4 with glacial acetic acid |
| Organic extraction | 2-butanol/suspension (v/v) |
| Acid precipitation | pH 6.2; 2 mM DTT; 0.1% SDS |
| Centrifugation | 10,000-14 15,000 xg |
| Acid precipitate solubilization | 2% SDS; 5 mM EDTA; 50 mM phosphate buffer |
| Reduction | 20 mM DTTA; pH 8.5; heat to 50° for 10 min. under nitrogen; cool to about 25° C. |
| Sepharcryl ® S200 column | 50 mM acetate; pH 5.5; 1% SDS; 1 mM EDTA |
| Oxidation | Iodosobenzoic acid (IBA) equimolar; protein; IBA; 0.1% SDS; 2 mM sokium pyrophosphate; pH 9; 1 mM EDTA |
| Concentration | pH 5.5 |
| Sephacryl ® Concentration | 50 mM acetate; pH 5.5; 0.1% SDS; 1 mM EDTA |
| Sephadex ® G-75 column | 50 mM acetate; pH 5.5; 0.1% SDS; 1 mM EDTA |
| Sephadex ® G-25 column | 0.1% sodium laurate (transfer componenet) in 10 mM Tris-HCl, |

| FlowChart 1 (continued) | |
|---|---|
| pH Adjustment | pH 9.2<br>pH of eluate lowered quickly with 1.0 N HCl to pH 3; sodium laurate precipitates |
| Centrifugation and Filtration | To remove the precipitated sodium laurate |
| Stabilization | 25% (v/v) glycerol or PEG 300 added in 20 mM NaPO$_4$ |

Flow Chart 1 illustrates the details of the individual process steps of a preferred embodiment of the present invention, including the culture of the transformed microorganisms in an appropriate fermentation medium through the final step where the purified IFN-$\beta$ is stabilized as a therapeutic formulation. The individual process steps of such an example of one embodiment of the instant invention are summarized as follows:

(a) growing the transformed bacterial hosts in an appropriate fermentation medium;

(b) concentrating the bacteria in the fermentation medium by cross-flow filtration, centrifugation or other conventional methods;

(c) disrupting the cell wall and cell membrane of the bacteria;

(d) removing greater than 99% by weight of the salts from said disruptate by diafiltration or centrifugation;

(e) redisrupting the desalted disruptate;

(f) adding a material to the disruptate to increase the density or viscosity of, or to create a density or viscosity gradient in, the liquid within the disruptate;

(g) separating the refractile material from the cellular debris by high-speed centrifugation;

(h) solubilizing the refractile material in an aqueous buffer containing a reducing agent;

(i) organically extracting the solubilized refractile material, preferably with 2-butanol or 2-methyl-2-butanol;

(j) isolating said refractile material from the extractant, preferably by employing an acid precipitation step followed by centrifugation;

(k) solubilizing the resulting IFN-$\beta$ particle pellet with an aqueous solution of SDS at an IFN-$\beta$ to SDS ratio of about 1:3;

(l) reducing the solubilized IFN-$\beta$;

(m) purifying the reduced IFN-$\beta$ by chromatography;

(n) oxidizing the IFN-$\beta$ from step m;

(o) further purifying the oxidized IFN-$\beta$ by gel chromatography and collecting the eluate containing the purified IFN-$\beta$;

(p) desalting the purified IFN-$\beta$ eluate in a desalting column equilibrated and run in 0.1% sodium laurate in 10 mM Tris-HCl at a pH of from about 9.0 to about 9.8;

(q) lowering the pH of the eluate quickly to a pH range of from about 2 to about 4 with an appropriate acidic agent;

(r) centrifuging and filtering the IFN-$\beta$ pool; and (s) adding an effective amount either of glycerol or of PEGs having an average molecular weight of from about 190 to about 1600 daltons to stabilize/solubilize the IFN-$\beta$.

Ten mM dithiothreitol may be optionally included in the initial solubilization step, and the mixture may be heated to about 50° C. for about 10 minutes. In addition, the IFN-$\beta$ is preferably oxidized so that its cysteine residues are bridged to form cystines, as described by U.S. Pat. No. 4,530,787 to Shaked et al., using o-iodosobenzioc acid solution or by U.S. Pat. No. 4,572,798 to Koths et al., entitled "Method for Promoting Disulfide Bond Formation in Recombinant Proteins," using copper chloride. Preferably, o-iodosobenzioc acid is employed for the oxidation.

Herein incorporated by reference is the disclosure of EP published application No. 206,828 which details the procedure for extracting and purifying recombinant protein, such as IFN-$\beta$, which are deposited within the microbial host in refractile bodies. Said disclosure focuses on the isolation of the refractile materials by front-end processes which are termed either "abbreviated" or "expanded". A synopsis of said procedures follows.

The transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. [See *Review of Medical Biology*, Lange Medical Publications, 14th Ed pp. 80–85 (1980).] In expression vectors involving the trp promoter, the tryptophan concentration in the medium is carefully controlled to become limiting at the time IFN-$\beta$ expression is desired. Growth media for *E. coli* are known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by cross-flow filtration, centrifugation, or other conventional methods. Preferably a compound which is non-toxic to humans, such as 1-octanol, in an amount of about 1% by weight of total components, is added to the fermenter before or during cell concentration to ensure that no viable recombinant organisms remain before containment is broken.

Following concentration of the harvested culture, the cell walls and membranes of the microorganisms are disrupted. Conventional cell disruption techniques such as homogenization, sonication, or pressure cycling may be used in this step of the precess. Preferred methods are sonication or homogenization with a homogenizer. The end point of the disruption step can be determined by monitoring the optical density with the absorbance at 260 nm of the suspension typically increasing with cell lysis. In any event, the disruption should break substantially all of the cells so that substantially no intact cells are carried through to the solubilization step. Before the disruption, the pH of the liquid phase of the concentrate is adjusted, if necessary, to a level that facilitates removal of *E. coli* proteins in subsequent steps, while retaining the heterologous protein as an insoluble complex in the cellular debris.

After the cells have been disrupted, deionized water is preferably added to the disruptate and greater than 99% by weight of the salts are removed therefrom. The removal of these salts to reduce the ionic strength of the disruptate may be accomplished by diafiltration using deionized water to flush out the ions or by centrifuging to pellet the cellular debris and refractile bodies followed by resuspension in deionized water.

After the salts are essentially removed, optionally a compound such as 1-octanol may be added to the desalted disruptate, if not added earlier, to ensure that no viable recombinant organisms remain. The desalted disruptate is again disrupted as described above for the initial disruption.

After redisruption, density or viscosity is increased and/or a gradient is created during centrifugation in the liquid within the disruptate by adding a material to the disruptate.

In the final step of the abbreviated "front-end" process to recover the refractile bodies, the refractile bodies containing the desired protein are separated from the cellular debris by high-speed centrifugation. By "high-speed centrifugation" is meant spinning the suspension in a centrifuge at about 10,000 to 40,000 times gravity, preferably about 10,000–20,000× g, for a suitable time period depending on the volume, generally about 10 minutes to seventy-two hours. The pellet resulting from the centrifugation is called the "particle pellet" or "particle paste".

In an alternative, expanded "front-end" process to recover the refractile bodies, the particle pellet obtained from the last centrifugation step of the abbreviated front-end process, is solubilized, reduced and then extracted from the aqueous medium with 2-butanol or 2-methyl-2-butanol. The extractant phase is then precipitated with an acid and centrifuged to produce a "final pellet" or "final paste" which is then further purified as indicated.

The alternative, expanded front-end process is distinguished from the abbreviated front-end process in that it comprises several additional steps as follows: solubilizing the refractile bodies under reducing conditions; organically extracting the solubilized refractile material; and isolating said refractile material from the extractant. Essentially, the enhanced purity of the final pellet as opposed to the particle pellet lessens the purifying burden of downstream processing. There is an interdependence between the choice of the front-end process and later process purification steps to achieve the desired purity level for the final product. Once the choice of the particular front-end recovery of the refractile bodies has been made, one skilled in the art can pick and choose the alternative purifying steps outlined below to achieve the desired purity level of the final product.

Whether the abbreviated or expanded front-end process is utilized to recover the refractile bodies containing the IFN-$\beta$, the next step in purification is solubilizing either the particle or final pellet containing the refractile material. The following solubilizing agents can be used: sodium dodecyl sulfate (SDS), sodium laurate, sodium dodecyl sulfonate, sodium decyl sulfate, sodium tetradecyl sulfate, sodium tridecyl sulfonate, sodium dodecyl N-sarcosinate, sodium tetradecyl N-sarcosinate, sodium dioctylsulfosuccinate, and guanidine hydrochloride. Preferred solubilizing agents are SDS, sodium laurate or guanidine hydrochloride.

The solubilizing agent is in an aqueous buffer, preferably phosphate buffered saline. The preferred percentage of the solubilizing agent is in the range of about 1% to about 5% (w/v). (Percentages herein reflect weight to volume ratios.)

Reducing agents that can be employed during the solubilization step include: $\beta$-mercaptoethanol ($\beta$-mer), glutathione, cysteine and dithiothreitol (DTT). DTT and $\beta$-mer are the most preferred reducing agents.

The solubilization will typically be carried out at temperatures in the range of 20° C. to 25° C. with mixing to facilitate contact between the solid phase and the solubilizing medium. Optionally, a reduction step may be carried out at this point. The pH, if necessary, may be adjusted to a range of 8.5 to 10, most preferably approximately 9. The suspension may be heated to 50°±5° C. for 5 to 15 minutes under nitrogen. The reaction mixture would then be cooled to approximately 25° C.

The solubilization is considered complete when the sample has sat 15 minutes or the solution turns translucent. Optionally at this point, the insoluble material may be separated by centrifugation or filtration after completing the solubilization.

After the protein is solubilized, the resulting suspension may optionally centrifuged at 10,000–40,000× g, preferably 10,000 to 15,000× g, to obtain a pellet containing, inter alia, additional host (e.g., *E. coli*) proteins, notably including certain contaminants that have molecular weights very close to that of the desired protein. The exact speed of centrifugation is not critical, as most of the insoluble material will come out, even at low speeds. The pellet is discarded and the supernatant containing the desired protein is retained and processed to recover the desired protein.

If a reduction step was not carried out during the solubilization, the next step in the process would be a reduction of the solubilized refractile body protein. A preferred reducing agent is dithiothreitol (DTT). Reduction conditions may also include the addition of a chelating agent such as ethylene- diaminetetraacetic acid (EDTA).

The next step in the process is to separate the protein in the supernatant from any host contaminants remaining after centrifugation or filtration and optimally from the solubilizing agent. Gel filtration chromatography, reverse-phase high performance liquid chromatography (RP-HPLC), or a combination of gel filtration chromatography and RP-HPLC, can be used. The gel filtration chromatography is preferably carried out in two stages that remove both pyrogenic components and protein contaminants having molecular weights higher or lower than that of the protein. Gels that are capable of fractionating the solution to permit separation of the protein from these contaminants are commercially available. Sephacryl® S-200 is a preferred gel for removing the higher molecular weight components and Sephadex® G-75 or G-100 gels are preferred for removing the low molecular weight contaminants. The gel filtrations will typically be run in buffered solutions (pH 5.5 to 7.0) containing about 0.1% to 1.5% solubilizing agent and about 0.5 to 10 mM reducing agent. The column will be sized to permit suitable resolution of the desired components.

RP-HPLC is an alternative to gel filtration. Also, RP-HPLC is capable of removing molecules from the solution that have molecular weights close to the protein and cannot, therefore, be removed completely by gel filtration. In addition, contaminants such as bacterial endotoxin are also removed effectively by RP-HPLC. Therefore, RP-HPLC may also be used as a final purification step after gel filtration.

Co-pending, commonly owned U.S. application Ser. No. 946,083 filed Dec. 23, 1986 entitled "Purification of Recombinant Beta-Interferon Incorporating RP-HPLC" concerns reverse-phase high performance liquid chromatography (RP-HPLC) methods for purifying recombinant beta-interferon and processes for purifying recombinant beta-interferon incorporating said RP-HPLC methods. Said application is herein incorporated by reference.

It is preferred in carrying out the process of this invention that the last step of purification before stabilization of the formulation is a desalting step employing a transfer component, such as sodium laurate at a pH range of about 8.5 to about 10. This highly pure material contains less than about 2 ng endotoxin, usually less than about 0.01 ng endotoxin, per 100,000 units protein bioactivity.

Co-pending, commonly owned U.S. application Ser. No. 048,686 filed May 11, 1987, concerns a process to obtain purified, biologically active, bacterially produced IFN-$\beta$, wherein the process comprises subjecting reduced, solubilized, bacterially produced IFN-$\beta$ in a chaotropic environment to oxidizing conditions and then removing the chaotropic environment in the presence of an effective amount of a solubilizing additive. Said application is herein incorporated by reference.

The formulation of the protein in accordance with this invention is then carried out as described in detail above. It may be carried out as a separate operation using purified, selectively oxidized protein or in an operation that is integrated with the purification of the selectively oxidized protein. In the latter case, the starting material for the formulation is a protein-containing product from a RP-HPLC treatment of the selectively oxidized product. Preferably a product selectively oxidized by the RP-HPLC product (pool) will comprise a solution of the protein in a water-organic solvent mixture. The nature of the organic solvent will depend upon the solvent system used in RP-HPLC. Examples of systems that maybe used are combinations of an organic acid such as acetic acid, trifluoroacetic acid or heptafluorobutyric acid, and an organic solvent such as propanol or acetonitrile.

This invention can also be considered to include methods for screening other polyhydric non-detergent solubilizer/stabilizers, such as glycerol and the above described PEGs, for inclusion in prototype formulations.

A preferred and representative example of such a screening method comprises the steps of:

(a) passing extracted, purified recombinant IFN-$\beta$ in 0.1% SDS on a desalting column equilibrated in 0.1% sodium laurate in an elution buffer at pH 9.0-10.0;

(b) lowering the pH of the eluate with an appropriate acidic agent to from about pH 2 to about pH 4;

(c) adding an appropriate concentration of a candidate polyhydric non-detergent solubilizer/stabilizer or combination of polyhydric non-detergent solubilizer/stabilizers;

(d) allowing said solution to stand for from about twenty-four hours to about one month at about 4° C.; and (e) observing whether the solution remains stable or not. If the solution remains stable, and the recombinant IFN-$\beta$ retains its bioactivity, the polyhydric non-detergent candidate or combination of such candidates is considered to be within the scope of the solubilizer/stabilizers of this invention.

The term purified recombinant IFN-$\beta$ in the screening step (a) above preferably refers to IFN-$\beta$ that has been purified according to the procedures described in Example 1 below and outlined in Flow Chart 1 through the sizing step of the G-75 column. However, such a screening method is exemplary and other screening methods employing other methods of purifying recombinantly produced IFN-$\beta$ are within the scope of this invention.

If the candidate solubilizer/stabilizer or combination thereof maintains the recombinant IFN-$\beta$ in solution at a pH range from about 2 to about 4 for one month at 4° C. it is considered for inclusion in the prototype formulations of this invention.

A preferred screening process includes the step of filtering from the desalted IFN-$\beta$ pool the precipitated sodium laurate which precipitates in step (b). The elution buffer of step (a) is preferably Tris-HCl, borate, phosphate, acetate or pyrophosphate, and is more preferably at pH 9.0 to 9.8.

To analyze prototype formulations, ultracentrifugation is used as a simple method of detecting the presence of high molecular weight aggregates. Such candidate formulations can also be screened by ultraviolet scans, turbility measurements, SDS-PAGE under non-reducing conditions and Western blots.

The formulations of this invention prepared as described above are suitable for parenteral administration to humans or other mammals in therapeutically effective amounts (i.e., amounts which eliminate or reduce the patient's pathological condition) to provide therapy thereto. IFN-$\beta$ therapy is appropriate for anti-cancer, anti-viral and anti-psoriasis treatment.

The formulations of this invention are useful for parenteral administration, for example, intravenous, intrathecal, subcutaneous, intraperitoneal, intramuscular, intraorbital, ophthalmic, intracapsular, intraspinal, intrasternal, topical, intranasal aerosol, scarification, and also, for oral administration. The preferred routes of administration are by intramuscular, subcutaneous and intravenous injection.

The following examples further illustrate the formulations and processes of the invention. These examples are not intended to limit the invention in any manner. In these examples all temperatures are in degrees Celsius unless otherwise indicated.

EXAMPLE 1

An analog IFN-$\beta$ designated IFN-$\beta_{ser17}$ was recovered from *E. coli*. The amino acid sequence of this recombinant IFN-$\beta$ is different from that of native human IFN-$\beta$ in that the cysteine at position 17 has been changed to serine. The strain of IFN-$\beta_{ser17}$-producing *E. coli* (K12/MM294-1) carrying plasmid pSY2501 used in this example was deposited at the American Type Culture Collection on Nov. 19, 1983 under accession No. 39,517. Said analog is described in U.S. Pat. Nos. 4,518,584 and 4,588,585 assigned to Cetus Corporation.

The *E. coli* thus transformed were grown in a 1000-liter fermenter at 37° C. The dissolved oxygen was maintained at about 40% by, as necessary: (1) increasing agitation; (2) adding air, and (3) adding oxygen.

Once the fermenter was filled with water to the operating volume, the following trace elements were added:

| | |
|---|---|
| $ZnSO_4 \cdot 7H_2O$ | 72 mM |
| $MnSO_4 \cdot 4H_2O$ | 30 µM |
| $CuSO_4 \cdot 5H_2O$ | 3 µM |
| $Na_3$ citrate$\cdot 2H_2O$ | 1.5 mM |
| $KH_2PO_4$ | 21 mM |
| $(NH_4)_2SO_4$ | 72 mM. |

The fermenter feed and addition vessels were then sterilized according to standard operating procedures. Then the following sterile additions were made:

| | |
|---|---|
| MgSO$_4$.7H$_2$O | 20 mM |
| FeSO$_4$.7H$_2$O | 100 µM |
| L-tryptophan | 70 mg/L |
| thiamine.HCl | 20 mg/L |
| glucose | 5 g/l. |

The fermenter was cooled and inoculated with frozen or seed *E. coli* culture at 2 mg/L. A glucose feed was employed to maintain the glucose concentration between 5-10 g/L. At approximately 15 hours after fermentation was begun, the pH was adjusted with KOH to 6.8. Optical density measurements and residual glucose measurements on samples were taken at 14-16 hours and approximately one hour intervals thereafter.

Induction of IFN-$\beta_{ser17}$ production by depletion of L-tryptophan from the culture medium occurred at about OD$_{680}$=10 followed by the addition of casamino acids to a final concentration of 2% at OD$_{680}$=15. The cultures were harvested when glucose consumption reached 40±6 g/l.

The refractile bodies containing the IFN-$\beta_{ser17}$ protein were then isolated. The harvested material was concentrated about 5-10 fold by circulating the harvest material under pressure through UF cross-flow filtration cartridges with a 100K molecular weight cutoff. Cells were disrupted by 3 passes through a Manton-Gaulin high-pressure homogenizer at 6,000 to 8,000 psig.

EDTA was added to the disruptate to a final concentration of 5 mM. The suspension was then diafiltered against 5 volumes of deionized water.

EDTA was then added to a final concentration of 2 mM. Octanol was added to 1% (v/v) to kill any residual live bacteria in the diafiltered product. The suspension was redisrupted by passing it twice through the Manton-Gaulin high-pressure homogenizer at 6,000-8,000 psig.

Sucrose was added to the redisruptate to a final concentration of 23% (wt/wt), creating a final density gradient between 1.1 and 1.25 g/ml. The mixture was centrifuged at 10,000 to 15,000× g, and the particle pellet or paste was collected. A temperature of at least 20° C. was maintained prior to and during centrifugation.

The particle pellet was then solubilized in phosphate buffered saline with 2% SDS. Solid DTT and EDTA were added to a final concentration of 10 mM and 2 mM, respectively. The suspension was heated to 50°±5° C. for 10 minutes under nitrogen. The reaction mixture was then cooled to approximately 25° C., and then the pH of the mixture was adjusted to 7.4.

A volume of 2-butanol equal to the total volume of the suspension was measured. The suspension and organic solution were pumped separately but simultaneously at flow rates of 1.1 to 1.3 liters per minute through a static mixer and then into a continuous centrifuge (Westfalia at approximately 11,770× g) for phase separation. The 2-butanol-rich phase containing the IFN-$\beta_{ser17}$ was collected (Organic Extract).

The 2-butanol extract was mixed with 2.5 volumes of 0.1% SDS in phosphate-buffered saline. Solid DTT was added to a final concentration of 2 mM. The pH of the organic extract/buffer solutions was adjusted to 6.2±0.1 with glacial acetic acid (Acid Precipitate).

The mixture was then centrifuged (Sharples centrifuge at 13,200× g) for approximately 2-6 hours, the supernatant was decanted, and the final pellet was then collected (Final Pellet) containing approximately 81% IFN-$\beta$. The final pellet containing the refractile material was then further purified by downstream processing.

The final pellet was then re-suspended with 2% SDS in 50 mM phosphate buffer and 5 mM EDTA. Solid DTT was added to a final concentration of 20 mM, and the pH was adjusted to 8.5 with NaOH. The suspension was heated to 50°±5° C. for 10 minutes under nitrogen, and then cooled to approximately 25° C. The pH was then adjusted to a pH of 5.5 with glacial acetic acid, and the solution was filtered through a 0.65 µm filter.

The filtrate was then processed by pre-column chromatography by loading a Sephacryl ® S200 column and collecting fractions into clean, depyrogenated vessels using an elution buffer that is composed of 50 mM acetate, pH 5.5, 1 mM EDTA and 1% SDS. The fractions containing the IFN-$\beta$ monomer were pooled.

The pre-column pool was then concentrated by using a hollow-fiber ultrafiltration unit with a 10K molecular weight cut-off.

The concentrated pre-column pool was then oxidized using o-iodosobenzoic acid (IBA). The oxidation was effected by adding equimolar amounts of protein and IBA into a reaction vessel containing 2 mM sodium pyrophosphate, 0.1% SDS and 1 mM EDTA. A 20 µM excess of IBA was present at the end of the oxidation. The pH was controlled at 9.0±0.1 with NaOH during oxidation, and adjusted to 5.5±0.2 with glacial acetic acid when the oxidation was completed.

The IFN-$\beta$ protein was then concentrated using a hollow-fiber ultrafiltration unit with a 10K molecular weight cut-off.

The protein was then loaded onto the main column (Sephacryl ® S200-A), and fractions were collected into clean, depyrogenated vessels using an elution buffer that is composed of 50 mM acetate, pH 5.5, 1 mM EDTA and 0.1% SDS.

A SDS-PAGE was performed on samples from each fraction tube starting from the beginning of the peak to be pooled to the end of the peak. Using the SDS-PAGE results, the fractions containing no high molecular weight contaminants were determined. Those fractions were then pooled.

The main column pool was then concentrated by using a hollow-fiber ultrafiltration unit with a 10K molecular weight cut-off.

The above procedure performed with the main column was repeated on a Sephadex ® G-75 column. Using the SDS-PAGE results, the fractions containing neither low nor high molecular weight contaminants were pooled.

The desalting step was then performed at pH 9.2 wherein 0.1% sodium laurate was used as a transfer component as follows. The pH was adjusted with an appropriate basic agent such as 1 mM NaOH.

A Sephadex ® G-25 column was then equilibrated with 0.1% sodium laurate in 20 mM sodium phosphate, pH 9.2 and loaded with the Sephadex ® G-75 pool containing 0.1% SDS. Using the process chromatogram, the IFN-$\beta_{ser17}$ peak was collected. The pH of the eluate was then lowered quickly with 1.0 N HCl to pH 3.0, which precipitated the sodium laurate, but left the IFN-$\beta_{ser17}$ in solution.

The mixture was centrifuged at 35,000× g for 30 minutes and the supernatant was filtered through a 0.22 micron nitrocellulose filter. SDS concentration was assayed by acridine orange. [Sokoloff et al., "Rapid Spectrophotometric Assay of Dodecyl Sulfate Using Acridine Orange," Anal. Biochem., 118:138-141 (1981).] The recovery of the IFN-$\beta_{ser17}$ was above 85%, and the SDS concentration was reduced to less than 10 μg/mg.

The filtered supernatant was then stabilized by adding either 25% glycerol (v/v) or 25% PEG 300.

The formulations were then observed to see if a precipitate formed. As noted in Table 1, no precipitate formed for either formulation within 5 minutes of their preparation.

The formulations were then kept at 4° C. for 24 hours, and then tested by ultracentrifugation. They were then tested again by ultracentrifugation at one week. Ultracentrifugation is a simple method of detecting the presence of high molecular weight aggregates and oligomers. Ultracentrifugation was performed in a Beckman L8-70 using a type 70.1 Ti rotor. Five milliliter samples of the formulated product were spun at 55,000 rpm for one hour. The supernatant was measured by absorbance at 280 nm. Said absorbance was then compared to that prior to centrifugation to determine the percent of IFN-$\beta$ recovered. The results are listed below in Table 1. The IFN-$\beta$ remained soluble in both representative formulations.

TABLE 1

Recovery of IFN-$\beta$ in the Supernatant

| Formulation | Precipitation at 5 minutes | % Recovery $A_{289}$ (24 Hours) | % Recovery by $A_{280}$ (1 Week) |
|---|---|---|---|
| pH 3 25% glycerol 25 mM NaPO$_4$ | 0 | 100 | 100 |
| pH 3 25% PEG 300 25 mM NaPO$_4$ | 0 | 100 | 100 |

The formulations were also tested by the cytopathic effect assay described by Steward, The Interferon System, p. 17 (1981), at time=0,24 hours, 48 hours and one week. Table 2 shows the results of such bioassay tests. The variability of the CPE assay is about plus or minus one log. Within the variability of the assay, the results for the control and for the formulated products are not significantly different. The representative formulations maintained bioactivity at 4° C. over the course of one week. The G-75 sample was taken from the eluate of the Sephadex ® G-75 column as described above.

TABLE 2

Specific Activity (CPE Assay) of Various Formulations (U/mg × 10$^7$)

| Sample | 0 Hours | 24 Hours | 48 Hours | 1 Week |
|---|---|---|---|---|
| G-75 | 18.5 | — | — | — |
| 25% glycerol 25 mM NaPO$_4$ pH 3 | 10.0 | 20.0 | 20.0 | 6.9 |
| 25% PEG 300 25 mM NaPO$_4$ pH 3 | 1.6 | 0.2 | — | 0.4 |

Deposits

As mentioned above, a culture of E. coli K12/MM294-1 carrying plasmid pSY2501 was deposited at the American Type Culture Collection (ATCC), 12301 Parklawn Drive, Rockville, MD 20852, U.S.A., on Nov. 18, 1983 under ATCC No. 39,517.

Said deposit was made pursuant to a contract between the ATCC and the assignee of this patent application, Cetus Corporation. The contract with the ATCC provides for permanent availability of said strain and progeny thereof to the public upon issuance of a U.S. patent related to this application describing and identifying the deposit or upon the publication or laying open to the public of any U.S. or foreign patent application, whichever comes first, and for the availability of the strain and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strain on deposit should die or be lost or destroyed when cultivated under suitable conditions, it will be promptly replaced upon notification with a viable culture of the same strain.

The deposit under the terms of the Budapest Treaty assure that said culture deposited will be maintained in a viable and uncontaminated condition for a period of at least five years after the most recent request for the furnishing of a sample of the deposited microorganism was received by the ATCC and, in any case, for a period of at least 30 years after the date of the deposit.

The culture was made available on May 21, 1985. Availability of the deposited strain is not to be construed as a license to practice the invention in contravention of the rights granted under the authority of any government in accordance with its patent laws.

Also, the present invention is not to be considered limited in scope by the strain deposited, since the deposited embodiments are intended only to be illustrative of particular aspects of the invention. Any microorganism strain which is functionally equivalent to those deposited are considered to be within the scope of this invention. Further, various modifications of the invention in addition to those shown and described herein apparent to those skilled in the art from the preceding description are considered to fall within the scope of the appended claims.

What is claimed is:

1. A stable pharmaceutical composition of matter suitable for parenteral administration to mammals that is at a pH range of from about 2 to about 4 comprising a therapeutically effective amount of a recombinant interferon-$\beta$ protein dissolved in an inert carrier medium comprising as a stabilizer/solubilizer an effective amount of polyethylene glycol polymers having an average molecular weight from about 190 to about 1600 daltons in the substantial absence of detergents and at a pH between 2 and 4.

2. A composition according to claim 1 wherein the concentration range (v/v) for said stabilizer/solubilizer is from about 5% to about 50%.

3. A composition according to claim 2 wherein said concentration range is about 25%.

4. A composition according to claim 2 wherein the stabilizer/solubilizer is polyethylene glycol polymers having an average molecular weight of from about 190 to about 420 daltons.

5. A composition according to claim 4 wherein said polyethylene glycol polymers have an average molecular weight of about 285 to about 315 daltons.

6. A composition according to claim 5 wherein the stabilizer/solubilizer is PEG 300 and the recombinant interferon-$\beta$ protein is IFN-$\beta_{ser17}$.

7. A composition according to claim 6 wherein the concentration (v/v) of the PEG 300 is about 25%.

8. A composition according to claim 1 wherein the recombinant interferon-$\beta$ protein is IFN-$\beta_{ser17}$.

9. A composition according to claim 1 further comprising an effective amount of a buffer at a concentration from about 1 to about 50 mM.

10. A composition according to claim 9 wherein the concentration of the buffer is from about 10 to about 25 mM.

11. A composition according to claim 1 wherein the pH range is from about 2.5 to about 3.5.

12. A composition according to claim 11 wherein the pH range is about 3.

13. A composition according to claim 10 wherein the buffer is selected from the group consisting of phosphoric acid, glycine and citric acid.

14. A composition according to claim 13 herein the buffer is phosphoric acid.

15. A stable pharmaceutical composition of matter suitable for parenteral administration to mammals that is at a pH range of from about 2 to about 4 comprising a therapeutically effective amount of a recombinant IFN-$\beta$ protein dissolved in an inert carrier medium comprising an effective amount of a non-detergent polyhydric stabilizer/solubilizer or a combination of polyhydric non-detergent stabilizer/solubilizers selected according to a screening method comprising:
    (a) purifying recombinant IFN-$\beta$;
    (b) lowering the pH of the IFN-$\beta$ to between 2 to 4;
    (c) adding a non-detergent solubilizer or combination of nondetergent solubilizers; and
    (d) evaluating whether the IFN-$\beta$ remains in solution.

16. A stable pharmaceutical composition of matter suitable for parenteral administration to mammals that is at a pH range of from about 2 to about 4 consisting of a therapeutically effective amount of a recombinant interferon-$\beta$ protein dissolved in an inert carrier medium comprising as a stabilizer/solubilizer an effective amount of polyethylene glycol polymers having an average molecular weight from about 190 to about 1600 daltons in the substantial absence of detergents and at a pH between 2 and 4.

* * * * *